(12) United States Patent
Silverman et al.

(10) Patent No.: US 8,420,574 B2
(45) Date of Patent: Apr. 16, 2013

(54) PLANT GROWTH ENHANCEMENT WITH COMBINATIONS OF PESA AND HERBICIDES

(75) Inventors: Franklin Paul Silverman, Highland Park, IL (US); Jennifer C. Kochan, Palatine, IL (US); Dale O. Wilson, Jr., Round Lake Beach, IL (US); Nicole Higgs, Racine, WI (US); Asako Iida, Hyogo (JP); Peter D. Petracek, Grayslake, IL (US); Gregory D. Venburg, Deerfield, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 223 days.

(21) Appl. No.: 12/763,642

(22) Filed: Apr. 20, 2010

(65) Prior Publication Data
US 2010/0267556 A1 Oct. 21, 2010

Related U.S. Application Data

(60) Provisional application No. 61/170,752, filed on Apr. 20, 2009.

(51) Int. Cl.
*A01N 37/10* (2006.01)
*A01N 43/00* (2006.01)
*A01N 43/48* (2006.01)
*A01N 25/32* (2006.01)

(52) U.S. Cl.
USPC ............ 504/321; 504/103; 514/131; 424/406

(58) Field of Classification Search .................. 504/321, 504/103; 514/131; 424/406
See application file for complete search history.

(56) References Cited

U.S. PATENT DOCUMENTS

| 4,528,020 | A  | * | 7/1985  | Kolc et al. ........................ 71/28 |
| 6,617,280 | B2 | * | 9/2003  | Fafchamps et al. ........... 504/127 |
| 6,660,692 | B1 |   | 12/2003 | Hewett |
| 2007/0197391 | A1 |   | 8/2007  | Clark et al. |

FOREIGN PATENT DOCUMENTS

| WO | WO 99/45774      |   | 9/1999 |
| WO | WO 9945774 A1    | * | 9/1999 |

OTHER PUBLICATIONS

Itagaki et al., "Biological activities and structure-activity relationship of substitutation compounds of N-[2-(3-indolyl)ethyl]succinamic acid anf N-[2-(1-naphthyl)ethyl]succinamic acid, derived from a new category of root-promoting substances, N-(phenethyl)succinamic acid analogs", Plant and Soil 2003, 255: pp. 67-75.

* cited by examiner

*Primary Examiner* — Fereydoun G Sajjadi
*Assistant Examiner* — Courtney Brown
(74) *Attorney, Agent, or Firm* — Wood, Phillips, Katz, Clark & Mortimer

(57) ABSTRACT

N-(phenylethyl)succinamic acid or its salts is applied as a seed treatment or applied directly on or near the root zone of the seedling or growing plant to protect plant growth in the presence of selected herbicides.

5 Claims, No Drawings

PLANT GROWTH ENHANCEMENT WITH COMBINATIONS OF PESA AND HERBICIDES

FIELD OF THE INVENTION

The present invention is directed to improving plant growth using N-(phenylethyl)succinamic acid (PESA) or its salts to protect target plants from an herbicide. This is accomplished using a treatment of N-(phenylethyl)succinamic acid or its salts when an herbicide is used, where PESA is applied as a seed treatment or applied directly to or near the root zone of a seedling or growing plant, and protects against the growth inhibition caused by an herbicide

BACKGROUND OF THE INVENTION

N-(2-phenylethyl)succinamic acid (PESA) is taught as an active ingredient of a plant growth regulator in WO 99/45774, which describes that amido acids including N-(phenylethyl) succinamic acid (PESA) are root growth promoters.

A variety of herbicides are used to kill unwanted plants (weeds) in crop fields, lawns, greenhouses or orchards. Typically, these herbicides are sprayed and subsequently incorporated into the soil (pre-emergence) or onto the plants (post-emergence).

Herbicides can be expensive, and their use may result in unintended consequences such as groundwater contamination, crop damage, environmental damage, spray drift, and human and mammalian health concerns. In particular, protection of young seedlings and plants from pre-emergence herbicides would reduce or avoid unintended herbicidal effects such as delayed early growth and stunting.

There are many classes of herbicides that may be grouped based on their mode of action. One class of herbicides of particular interest is dinitoanalines. These compounds inhibit the assembly of microtubules, and consequently inhibit cell division. These compounds are active on grasses and small-seeded broadleaf weeds. Examples of this class of herbicides are trifluralin and pendimethalin. Trifluralin is marketed in the US under the trade name Treflan® (Dow Agrosciences, Indianapolis, Ind. USA), while pendimethalin is marketed under the trade name Prowl® (BASF Agricultural Products, Research Triangle Park, N.C. USA). Another class of herbicides of interest is pyridines, which inhibit cell division at the growing points in both the roots and shoots of target plants. An example of a pyridine herbicide is dithiopyr, which is marketed in the US as Dimension® (Dow Agrosciences, Indianapolis, Ind. USA).

Several other classes of herbicides are of commercial importance and are also of interest insofar as one can protect crop plants from them without negatively affecting their herbicidal activity on weeds. These include inhibitors of acetyl-CoA carboxylase, such as clodinafop-propargyl, inhibitors of plant cell division, such as metolachlor; auxinic herbicides, such as dicamba, and protoporphyrinogen oxidase inhibitors such as flumioxazin.

It is an object of the present invention to protect or safen crops, turf or ornamental plants from unintended herbicidal consequences of herbicide application. It is also an object of this invention to lessen the effects of spray drift on non-target species when these herbicides are used.

SUMMARY OF THE INVENTION

The present invention is directed to a composition for improving plant growth using N-(phenylethyl)succinamic acid or its salts, when an herbicide is used. This is accomplished by using N-(phenylethyl)succinamic acid or its salts as a seed treatment or by application directly on or near the root zone of a seedling or growing plant. Alternatively, PESA may be applied to the shoots or leaves of the plant. Because the herbicide treatments may differentially affect the root and shoot of the plant, less than optimal growth results in an imbalance of the root to shoot ratio. This invention may permit the use of PESA with herbicides to maintain optimal plant growth.

DETAILED DESCRIPTION OF THE INVENTION

Herbicides are compounds used to kill unwanted plants (weeds) in crop fields, lawns, greenhouses or orchards. Typically, herbicides are sprayed and subsequently incorporated into the soil (pre-emergence) or onto the plants (post-emergence). Herbicides are generally specific in their mode-of-action.

Suitable herbicides include but are not limited to, dinitroanilines, pyridines, aryloxyphenoxypropionates, chloroacetoamides, benzoic acids, and dicarboximides.

PESA is N-(2-phenylethyl)succinamic acid of the formula:

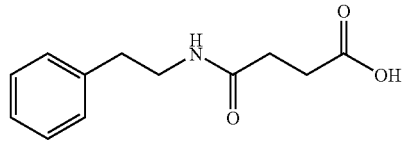 [SMILES: O=C(O)CCC(=O)NCCc1ccccc1]

In the present invention, any pesticidally acceptable salt of PESA can also be used as well as PESA. Examples of such salts include calcium, magnesium, potassium, sodium, or ammonium. The organic ammonium salts include the salts formed by neutralization of PESA by an amine bearing one, two or three groups selected from the group consisting of C1-C4 alkyl groups and C1-C4 hydroxyalkyl groups. Typical examples of organic ammonium salts include the trimethylammonium salt, isopropylammonium salt, 2-hydroxyethylammonium salt (ethanolamine salt), 2-hydroxyethyldimethylammonium salt (dimethylethanolamine salt), bis(2-hydroxyethyl)ammonium salt (diethanolamine salt) and tris (2-hydroxyethyl)ammonium salt (triethanolamine salt). The presently preferred salt is the sodium salt.

The salts of PESA are produced, for example, by dissolving the free acid (PESA) in water and adding an equimolar amount of a base to the solution. In the case of the sodium salt, sodium hydroxide is preferably used as the base and this method allows for the production of sodium salt solution ranging in concentration from 0.1 to 40%.

The compositions of this invention comprise a herbicidal compound and PESA or its salts. The amount of PESA or its salts in the composition is an amount effective for enhancing the activity of the herbicide while maintaining root and shoot growth, and is usually between 0.5 and 99 times by weight of the amount of the herbicide used. The amount of the herbicide is usually 0.3 to 30% by weight, and the amount of PESA or its salts is usually 0.02 to 20% by weight of the composition.

The composition further comprises a carrier, and optionally comprises auxiliaries for incorporation into the formulation. Examples of such auxiliaries include surfactants, dispersing agents, thickeners, stabilizing agents, antifreezing agents and colorants.

Examples of solid carriers include powders and granules of clays such as kaoline clay, diatomaceous earth, bentonite, fubasami clay and terra alba; synthetic hydrated silica; talc;

ceramic; other inorganic minerals such as sericite, quartz, sulfur, activated carbon, calcium carbonate and hydrated silica; and chemical fertilizers such as ammonium sulfate, ammonium phosphate, ammonium nitrate, ammonium chloride and urea. Examples of liquid carries include aromatic and aliphatic hydrocarbons such as xylene, toluene, alkylnaphthalene, phenylxylylethane, kerosene, gas oil, hexane and cyclohexane; halogenated hydrocarbons such as chlorobenzene, dichloromethane, dichloroethane and trichloroethane; alcohols such as methanol, ethanol, isopropyl alcohol, butanol, hexanol, benzyl alcohol and ethylene glycol; ethers such as diethyl ether, ethylene glycol dimethyl ether, diethylene glycol monomethyl ether, diethylene glycol monoethyl ether, propylene glycol monomethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrlile and isobutyronitrile; sulfoxides such as dimethyl sulfoxide (DMSO); amides such as N,N-dimethylformamide, N,N-dimethylacetamide and N-methylpyrollidone; alkylydene carbonates such as propylene carbonate; vegetable oils such as soybean oil and cotton seed oil; plant essential oils such as orange oil, hyssop oil and lemon oil; and water. Examples of gaseous carriers include butane gas, flon gas, liquefied petroleum gas (LPG), dimethyl ether and carbon dioxide. When the herbicidal composition contains a carrier, the amount of the carrier is usually 1 to 99% by weight of the herbicidal composition.

Examples of surfactants include alkylsulfate salts, alkylsulfonate salts, alkylarylsulfonate salts such as alkylbenzenesulfonate salts and alkylnaphthalenesulfonate salts, polyoxyethylene alkyl ether phosphate salts, alkylaryl ethers, polyoxyethylene alkylaryl ethers, polyethylene glycol ethers, polyvalent alcohol esters and sugar alcohols. Examples of dispersing agents include calcium ligninsulfonate, methylcellulose and hydroxymethylcellulose.

Examples of thickeners include aluminum magnesium silicate, gum arabic, polyvinyl alcohol and polyvinylpyrrolidone.

Examples of stabilizing agents include BHT (2,6-di-tert-butyl-4-methylphenol) and BHA (mixture of 2-tert-butyl-4-methoxyphenol and 3-tert-butyl-4-methoxyphenol).

Examples of antifreezing agents include ethylene glycol, propylene glycol, trimethylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like, diethylene glycol, triethylene glycol, tetraethylene glycol, polyoxyethylene or polyoxypropylene glycols of molecular weight up to about 4000, diethylene glycol monomethyl ether, diethylene glycol monoethyl ether, triethylene glycol monomethyl ether, butoxyethanol, butylene glycol monobutyl ether, dipentaerythritol, tripentaerythritol, tetrapentaerythritol, diglycerol, triglycerol, tetraglycerol, pentaglycerol, hexaglycerol, heptaglycerol and octaglycerol.

Examples of colorants include azo dyestuffs and anthraquinone dyestuffs. When the composition contains a colorant, the amount of the colorant is usually 0.01 to 1.0% by weight of the herbicidal composition.

The composition of the present invention is prepared by conventional methods, for example, by mixing a herbicide compound, PESA or its salt, a carrier and optionally auxiliaries, and further pulverization, granulation and so on. The herbicidal composition of the present invention can be a variety of formulations: dry flowables (DF), liquid flowables (LF), true liquids (TL), emulsifiable concentrates (EC), dusts (D), wettable powders (WP), suspoemulsions (SE), water-dispersible granules (WG) and others. Some are registered for use only by commercial applicators using closed application systems, others are readily available for on-farm use as dusts, slurries, water soluble bags, or liquid ready-to-apply formulations.

The application dosage of the herbicidal composition of the present invention is usually 0.01 to 10.0 kg/km$^2$, preferably 0.05 to 5 kg/km$^2$ of the amount of the herbicidal compound.

The method of the present invention is a new use of PESA or its salts for protecting a plant from an herbicide by a treatment with PESA or its salts. It is performed by applying PESA or its salts to plants. The plant can be any part and in any stage, for example, seed, tuber, bulb, root, leaf, stem and sprout. PESA or its salts may also be applied to surroundings of the plant, for example, soil. The soil treatment can be performed by application on the soil surface, application by mixing with soil, or the like. PESA or its salts is used in an effective amount for protecting the plant from the herbicidal compound. The amount of PESA or its salts used in the invention depends on the kind of the herbicidal compound.

The method can be performed by applying the herbicide of the present invention to plants or surroundings of the plants Especially suitable target plants are potato, cereals (wheat, barley, rye, oats, rice), maize (corn), sugar beet, cotton, millet varieties such as sorghum, sunflower, bean, peas, oil plants (such as canola, rape and soybean), cabbage, tomato, eggplant, pepper, and other vegetables and spices, as well as woody perennials, ornamental shrubs, turf grass, and flowers.

Suitable target crops also include transgenic crop plants of the foregoing varieties. The transgenic crop plants treated according to the invention are plants, or propagation material thereof, which are transformed by recombinant DNA technology so that they are capable of synthesizing selectively acting toxins, such as, for example, from toxin-producing invertebrates, especially of the phylum Arthropoda; from *Bacillus thuringiensis* strains; from plants, such as lectins; or in the alternative, capable of expressing a herbicidal or fungicidal or abiotic stress resistance gene or capable of synthesizing a beneficial nutraceutical or pharmaceutical compound.

The compositions are particularly suited for applications on plant propagation material. The latter term embraces seeds of all kinds (fruit, tubers, grains), cuttings, cut shoots and the like. The preferred field of application is the treatment of all kinds of seeds (as specified in the target crops above), and in particular, the seed treatment of canola, maize, cereals, soybeans and other legumes and turfgrass.

A presently preferred application method of use of the composition of the present invention is seed treatment. Further, a presently preferred application method of PESA or its salts in the method of the present invention is also seed treatment. In seed treatment, the application amount of the composition of the present invention is usually 1 to 200 g, preferably 5 to 100 g per 100 kg of seeds in the amount of the herbicidal compound.

Procedure for Treating Samples of Seed in the Laboratory

Seed was sieved with a screen of mesh size appropriate to remove broken seeds and small trash. Cracked or otherwise damaged seeds were removed. The seed was well mixed, and 50 g samples were weighed into small plastic trays. Seed treatment slurries were made by adding measured amounts of PESA or its salts and other AIs to sufficient water to bring them up to a standard volume, typically 2 ml. A fungicide (Maxim XL; Syngenta Agricultural Products, Greensboro, N.C.), a polymeric binder (CF-Clear; Becker-Underwood, Ames, Iowa), and a colorant (Color Coat Red; Becker-Underwood, Ames, Iowa) were also included in the slurry at label rates. A small aliquot of this slurry was applied to the seed using the Hege 11 coater (Wintersteiger, Salt Lake City, Utah) with a six-inch bowl at a slurry rate of 30 ounces per 100 lbs of seed. The slurry was deposited drop-wise on the spinning disk atomizer using a syringe.

After treatment, each seed sample was placed in plastic trays and dried at a room temperature for 20 to 60 minutes. The samples were then placed in small plastic bags. Samples were spot-checked using a water activity meter to make sure the water activity is below 0.7.

Alternatively, PESA salt and herbicides may be added separately to the sterile water in the growth pouch.

Pouch Assay

Seeds were placed in germination pouches consisting of germination paper hydrated with sterile water that was an insert in a gas-permeable 16×14 cm plastic pouch (CYG Pouch; Mega International, St. Paul, Minn.). In these examples, in pouch solution evaluation, PESA sodium salt or other active ingredients were added to the sterile water in the pouch. The pouches were arranged in a completely randomized block design in growth racks and placed in 19-liter polycarbonate food storage containers (Rubbermaid Commercial Products, Winchester, Va.). The sealed containers were held in an upright growth cabinet maintained at 25 C with a 12 hour light: 12 hour dark photoperiod. After 6 days, the containers were removed from the growth cabinet, and the lengths of the roots and shoot were measured.

Hydroponic Assay:

Where hydroponically-grown rice was used in studies, the seeds were pre-incubated in water at 30 C for 2 days to stimulate germination. Three seeds were placed on a float and cultivated hydroponically in a test tube (25 mm×200 mm), which contained 50 ml of Kimura B nutrient solution at ⅛th strength supplemented with herbicides and PESA sodium salt. The exposure of the roots to the light was prevented by wrapping the tubes with aluminum foil. The rice seedlings were incubated in a growth cabinet at 25 C under continuous light for 14 days, and the total root length and shoot length were measured. Total root length (cm) was the root length/plant determined following scanning with WinRhizo software (Regent Instruments INC, Toronto, Canada).

The following examples are intended to illustrate the present invention and to teach one of ordinary skill in the art how to make and use the invention. They are not intended to be limiting in any way.

EXAMPLES

Example 1

Growth of rice cv. Chemere in the presence of trifluralin caused a significant decrease in both root and shoot length (Table 1). When rice is grown in the presence of PESA salt, a significant increase in both root and shoot length is seen in the absence of trifluralin. In the presence of 100 ppm trifluralin, root length was reduced by 90 percent, while the presence of 30 ppm PESA with 100 ppm trifluralin largely protected the roots from the negative effects of trifluralin. Although growth of rice seedlings in the presence of PESA salt increased shoot length, PESA salt did not consistently overcome the negative effects of trifluralin on shoot length.

This shows that the combination of PESA salt with trifluralin protects or safens rice from the negative effects of the herbicide on root growth.

TABLE 1

Effect of PESA salt and trifluralin on main root length and shoot length (cm) of rice cv. Cheniere.

| Trifluralin (ppm) | Root Length (cm) 0 ppm PESA salt | Root Length (cm) 30 ppm PESA Salt | Shoot Length (cm) 0 ppm PESA salt | Shoot Length (cm) 30 ppm PESA Salt |
|---|---|---|---|---|
| 0 | 9.2 | 10.7 | 3.2 | 3.7 |
| 1 | 9.8 | 10.6 | 3.7 | 3.6 |
| 10 | 8.3 | 9.1 | 3.3 | 2.9 |
| 100 | 0.9 | 5.1 | 2.2 | 2.4 |

Rice cv. Chemere was treated with PESA sodium salt prior to growing in the pouch. The treated seeds were then grown in the pouch in a dose-dependent series of trifluralin concentrations (Table 2). The results were similar to those observed in the previous experiment; PESA salt seed treatment provides significant protection against intermediate rates of trifluralin (50 ppm). This confirms that seed treatment with the PESA salt protects or safens rice from the negative effects of trifluralin herbicide on root growth.

TABLE 2

Effect of seed treatment with PESA salt on effects of trifluralin on root length (cm) of rice cv. Cheniere.

| Trifluralin (ppm) | Root Length (cm) 0 g PESA salt/100 lbs of seed | 10 g PESA salt/100 lbs of seed | 25 g PESA salt/100 lbs of seed | 50 g PESA salt/100 lbs of seed |
|---|---|---|---|---|
| 0 | 9.8 | 10.7 | 10.1 | 10.3 |
| 50 | 0.9 | 4.6 | 5.2 | 6.0 |
| 100 | 0.1 | 0.3 | 0.3 | 0.3 |

Example 2

In pouch treatment evaluation, the growth of rice cv. Chemere in the presence of the herbicide pendimethalin caused a significant decrease in both root and shoot length (Table 3). When rice is grown in the presence of PESA salt, a significant increase in root length is observed. In the presence of both PESA and pendimethalin, root length was on average 20% greater than the root length with pendimethalin alone. In the presence of 100 ppm pendimethalin, root length was reduced by 70%; the addition of 30 ppm PESA increased root length by 25%. Growth in the presence of PESA salt only slightly affected shoot length, and PESA salt did not overcome the negative effects of pendimethalin on shoot growth.

This shows that the combination of PESA salt with pendimethalin protects or safens rice from the negative effects of the herbicide on root growth.

TABLE 3

Effect of PESA salt and pendimethalin on main root length and shoot length (cm) of rice cv. Cheniere.

| Pendamenthalin (ppm) | Root Length (cm) 0 ppm PESA salt | Root Length (cm) 30 ppm PESA salt | Shoot Length (cm) 0 ppm PESA salt | Shoot Length (cm) 30 ppm PESA salt |
|---|---|---|---|---|
| 0 | 8.5 | 10.1 | 3.4 | 3.6 |
| 10 | 8.3 | 9.4 | 3.4 | 3.2 |
| 100 | 2.5 | 3.1 | 1.0 | 1.0 |
| 500 | 0.5 | 0.6 | 0.5 | 0.5 |

In the pouch assay, the growth of rice cv. Chemere in the presence of pendimethalin caused a significant decrease in both root and shoot length (Table 3). When rice is grown in the presence of PESA salt, GA3, or a combination of PESA salt and GA3, a significant increase in root length is observed (Table 4). Only GA3 or a combination of GA3 and PESA salt resulted in an increase in shoot length. In the presence of pendimethalin, root length was decreased by 75%, while shoot length was decreased by 67%. The addition of PESA salt to pendimethalin resulted in roots of rice that were twice the length of those grown in pendimethalin alone, an indication of herbicide safening. GA3 in the growth medium was only marginally effective at protecting the roots and shoots from pendimethalin. The combination of GA3 and PESA salt with pendimethalin did not result in significantly increased safening than was additive of the two compounds.

TABLE 4

Effect of PESA salt and gibberellic acid (GA3) on effects of pendimethalin on root and shoot length (cm) of rice cv. Cheniere.

| Treatment | Root Length (cm) | | Shoot Length (cm) | |
| --- | --- | --- | --- | --- |
| | 0 ppm Pendi-methalin | 50 ppm Pendi-methalin | 0 ppm Pendi-methalin | 50 ppm Pendi-methalin |
| Control | 9.7 | 2.9 | 3.9 | 1.3 |
| 30 ppm PESA salt | 11.2 | 5.6 | 3.8 | 1.1 |
| 10 ppm GA3 | 10.8 | 2.7 | 7.7 | 1.5 |
| 30 ppm PESA salt and 10 ppm GA3 | 12.0 | 5.8 | 7.5 | 1.6 |

Rice cv. Chemere was seed treated in a factorial study with PESA sodium salt and GA3. It was then seeded onto soil which was previously sprayed with the pendimethalin herbicide Prowl H$_2$O® (BASF Agricultural Products, Research Triangle Park, N.C.). Emergence of rice seedlings was counted daily and showed that either PESA salt or GA3 alone could protect the rice seedlings from pendimethalin, particularly at the 2 pints/acre rate (Table 5). The combination of GA3 and PESA salt provided better protection from pendimethalin than either GA or PESA salt alone. This data confirms that seed treatment with the PESA salt and GA protects or safens rice from the negative effects of pendimethalin herbicide on plant growth.

TABLE 5

Effect of PESA salt and gibberellic acid (GA3) on effects of Prowl ® (pendimethalin) on emergence of rice cv. Cheniere.

| Treatment | Percent Emergence at 12 days after planting Prowl ® (Pendimethalin) | | | |
| --- | --- | --- | --- | --- |
| | Control | 0.25 pints/acre | 0.5 pints/acre | 2 pints/acre |
| Control | 84.5 | 81.3 | 80.0 | 49.0 |
| 1 g GA3 per 100 lbs of seed | 93.0 | 88.3 | 86.6 | 58.3 |
| 50 g PESA salt per 100 lbs of seed | 86.1 | 79.0 | 80.7 | 61.0 |
| 50 g PESA salt and 1 g GA3 per 100 lbs of seed | 88.0 | 81.3 | 87.0 | 63.4 |

Example 3

Growth of rice cv. Chemere in the presence of the herbicide dithiopyr caused a significant decrease in both root and shoot length (Table 6). In the presence of 10 ppm dithiopyr, root length was reduced by 30 percent, while the presence of 30 ppm PESA protected the roots largely from the negative effects of dithiopyr. Growth in the presence of PESA salt only slightly affected shoot length, and the combination of PESA salt with dithiopyr did not significantly alter the negative effects of dithiopyr on shoot length.

This shows that the combination of PESA salt with dithiopyr protects or safens rice from the negative effects of the herbicide on root growth.

TABLE 6

Effect of PESA salt and dithiopyr on main root length and shoot length (cm) of rice cv. Cheniere.

| Dithiopyr (ppm) | Root Length (cm) | | Shoot Length (cm) | |
| --- | --- | --- | --- | --- |
| | 0 ppm PESA salt | 30 ppm PESA salt | 0 ppm PESA salt | 30 ppm PESA salt |
| 0 | 9.5 | 12.2 | 4.0 | 4.2 |
| 1 | 10.0 | 11.4 | 4.3 | 4.0 |
| 10 | 6.7 | 9.1 | 3.5 | 3.7 |
| 100 | 0.4 | 0.4 | 1.2 | 1.1 |

Due to the negative effects of dithiopyr on plant growth, we tested a combination of GA3 with PESA sodium salt to determine if it could increase the lengths of rice roots and shoots (Table 7). The combination of PESA salt and GA3 provided greater benefits for root and shoot growth in the presence of dithiopyr than either compound alone.

TABLE 7

Effect of PESA salt and gibberellic acid (GA3) on effects of dithiopyr on root and shoot length (cm) of rice cv. Cheniere.

| Treatment | Root Length (cm) | | Shoot Length (cm) | |
| --- | --- | --- | --- | --- |
| | Control | 10 ppm Dithiopyr | Control | 10 ppm Dithiopyr |
| Control | 9.5 | 4.1 | 3.9 | 3.0 |
| 30 ppm PESA Salt | 10.7 | 6.4 | 3.6 | 2.8 |
| 10 ppm GA3 | 10.7 | 4.7 | 7.0 | 5.6 |
| 30 ppm PESA salt and 10 ppm GA3 | 11.3 | 7.5 | 7.3 | 5.7 |

In addition, rice seed treated in a factorial study with PESA and GA3 was tested for its ability to protect rice from the herbicide Dimension 2EW® (dithiopyr). After seed treatment, rice was seeded into soil previously treated with the dithiopyr herbicide Dimension®. The emergence of the rice seedlings was counted daily and showed that either PESA salt or GA3 alone could protect the rice seedlings from dithiopyr, particularly at the 0.25 and 0.5 pints/acre rate (Table 8). The combination of GA3 and PESA salt provided better protection from dithiopyr than either GA or PESA salt alone. This data confirms that seed treatment with the PESA salt protects or safens rice from the negative effects of dithiopyr herbicide on plant growth.

TABLE 8

Effects of PESA salt, gibberellic acid (GA3) and Dimension ® (Dithiopyr) on emergence of rice cv. Cheniere.

| | Percent Emergence at 12 days after planting Dimension ® (Dithiopyr) | | |
|---|---|---|---|
| Treatment | Control | 0.25 pints/acre | 0.5 pints/acre |
| Control | 72.1 | 44.9 | 7.0 |
| 1 g GA3 per 100 lbs of seed | 94.1 | 57.0 | 14.6 |
| 50 g PESA salt per 100 lbs of seed | 77.2 | 61.0 | 13.9 |
| 50 g PESA Salt and 1 g GA3 per 100 lbs of seed | 86.3 | 65.1 | 14.3 |

Example 4

In a hydroponic culture evaluation, the growth of rice cv. Nipponbare in the presence of the acetyl CoA carboxylase (ACCase) inhibitor clodinafop-propargyl caused a significant decrease in both root and shoot length (Table 10). In the presence of 3 ppm clodinafop-propargyl, root length was reduced by 91 percent, while the presence of 40 ppm PESA salt with 3 ppm clodinafop-propargyl protected the roots from the negative effects of the herbicide.

TABLE 10

Effect of PESA salt and clodinafop-propargyl on total root length and shoot length (cm) of rice cv. Nipponbare.

| | Total Root Length[1] (cm) | | Shoot Length (cm) | |
|---|---|---|---|---|
| Clodinafop-propargyl (ppm) | 0 ppm PESA salt | 40 ppm PESA Salt | 0 ppm PESA salt | 40 ppm PESA Salt |
| 0 | 52.1 | 193.9 | 10.6 | 13.3 |
| 0.3 | 45.3 | 202.6 | 10.2 | 14.3 |
| 1 | 11.5 | 110.5 | 10.9 | 13.6 |
| 3 | 4.7 | 44.3 | 7.5 | 11.8 |

[1]Total root length (cm) is the composite length of all roots on the plant.

Example 5

Metolachlor is an inhibitor of plant cell division. In rice, metolachlor had a strong negative impact on root length; at 10 ppm metolachlor, a 60% decrease in root length was observed. The presence of PESA salt with 10 ppm metolachlor partially protected primary root length (Table 11).

TABLE 11

Effect of PESA salt and metolachlor on main root length and shoot length (cm) of rice cv. Cheniere.

| | Root Length (cm) | | Shoot Length (cm) | |
|---|---|---|---|---|
| Metolachlor (ppm) | 0 ppm PESA salt | 30 ppm PESA salt | 0 ppm PESA salt | 30 ppm PESA salt |
| 0 | 9.3 | 10.9 | 3.7 | 3.7 |
| 1 | 8.2 | 8.6 | 3.6 | 3.9 |
| 10 | 3.7 | 4.4 | 0.9 | 0.9 |
| 100 | 1.6 | 1.7 | 0.6 | 0.6 |

Example 6

In hydroponic culture evaluation, the growth of rice cv. Nipponbare in the presence of dicamba caused a significant decrease in both root and shoot length (Table 12). In the presence of 0.1 ppm dicamba, root length was reduced by 87 percent, while the presence of 40 ppm PESA salt with 0.1 ppm dicamba largely protected the roots from the negative effects of dicamba, and total root length was increased by 61 percent as compared with untreated control. Growth in the presence of PESA salt also increased shoot length. In the presence of 0.1 ppm dicamba, shoot length was reduced by 61 percent, while the presence of 40 ppm PESA salt with 0.1 ppm dicamba largely protected the shoots from the negative effects of dicamba.

This shows that the combination of PESA salt with dicamba protects or safens rice from the negative effects of the herbicide on root and shoot growth.

TABLE 12

Effect of PESA salt and dicamba on total root length and shoot length (cm) of rice cv. Nipponbare.

| | Total Root Length[1] (cm) | | Shoot Length (cm) | |
|---|---|---|---|---|
| Dicamba (ppm) | 0 ppm PESA salt | 40 ppm PESA salt | 0 ppm PESA salt | 40 ppm PESA salt |
| 0 | 44.9 | 121.9 | 11.4 | 15.1 |
| 0.01 | 21.3 | 155.4 | 10.6 | 15.1 |
| 0.1 | 6.0 | 72.5 | 4.5 | 12.5 |
| 1 | 0.0 | 9.2 | 3.8 | 3.6 |

[1]Total root length (cm) is the composite length of all roots on the plant.

Example 7

In a hydroponic culture evaluation, the growth of rice cv. Nipponbare in the presence of the PPO inhibitor flumioxazin caused a significant decrease in both root and shoot length (Table 13). In the presence of 1 ppm flumioxazin, root length was reduced by 28 percent, while the presence of 40 ppm PESA salt with 1 ppm flumioxazin protected the roots from the negative effects of flumioxazin. Growth in the presence of the PESA salt also increased shoot length. In the presence of 1 ppm flumioxazin, shoot length was reduced by 64 percent, while the presence of 40 ppm PESA salt with 1 ppm flumioxazin largely protected the shoots from the negative effects of flumioxazin.

TABLE 13

Effect of PESA salt and flumioxazin on total root length and shoot length (cm) of rice cv. Nipponbare.

| | Total Root Length[1] (cm) | | Shoot Length (cm) | |
|---|---|---|---|---|
| Flumioxazin (ppm) | 0 ppm PESA salt | 40 ppm PESA salt | 0 ppm PESA salt | 40 ppm PESA salt |
| 0 | 52.1 | 193.9 | 10.6 | 13.3 |
| 0.1 | 41.5 | 132.6 | 10.7 | 12.3 |
| 0.3 | 64.1 | 102.8 | 11.0 | 10.3 |
| 1 | 14.5 | 53 | 3.8 | 7.5 |
| 3 | 15.7 | 24.4 | 5.9 | 6.5 |

[1]Total root length (cm) is the composite length of all roots on the plant.

Example 8

In hydroponic culture evaluation, the growth of rice cv. Nipponbare in the presence of imazosulfuron, an acetolactate synthase (ALS) inhibitor, caused a significant decrease in both root and shoot length (Table 14). In the presence of 0.1 ppm imazosulfuron, root length was reduced by 49 percent, while the presence of 40 ppm PESA salt with 0.1 ppm imazosulfuron largely protected the roots from the negative effects of imazosulfuron, and total root length was increased by 87 percent as compared with untreated control. Growth in the PESA salt also increased shoot length. In the presence of 1 ppm imazosulfuron, shoot length was reduced by 86 percent, while the presence of 40 ppm PESA salt with 1 ppm imazosulfuron largely protected the shoots from the negative effects of the herbicide.

This result indicates that the combination of PESA salt with imazosulfuron protects or safens rice from the negative effects of the herbicide on root and shoot growth.

TABLE 14

Effect of PESA salt and imazosulfuron on total root length and shoot length (cm) of rice cv. Nipponbare.

| Imazosulfuron (ppm) | Total Root Length[1] (cm) | | Shoot Length (cm) | |
|---|---|---|---|---|
| | 0 ppm PESA salt | 40 ppm PESA salt | 0 ppm PESA salt | 40 ppm PESA salt |
| 0 | 44.9 | 121.9 | 11.4 | 15.1 |
| 0.01 | 41.4 | 169.8 | 12.6 | 14.5 |
| 0.1 | 23.1 | 83.8 | 8.6 | 13.2 |
| 1 | 4.9 | 13.8 | 1.6 | 7.9 |

[1]Total root length (cm) is the composite length of all roots on the plant.

Example 9

The ability of PESA salts to protect plants from herbicidal compounds was not observed in the response of rice or cotton to the acetolactate synthase (ALS) inhibitor chlorsulfuron. In rice, chlorsulfuron had a strong negative impact on root length. Although PESA salt alone increased root length, it had no activity in combination with chlorsulfuron (Table 15).

TABLE 15

Effect of PESA salt and chlorsulfuron on main root length and shoot length (cm) of rice cv. Cheniere.

| Chlorsulfuron ppm | Root Length (cm) | | Shoot Length (cm) | |
|---|---|---|---|---|
| | 0 ppm PESA salt | 30 ppm PESA salt | 0 ppm PESA salt | 30 ppm PESA salt |
| 0 | 11.6 | 12.8 | 4.8 | 4.9 |
| 10 | 0.6 | 0.5 | 0.9 | 0.9 |
| 100 | 0.3 | 0.3 | 0.7 | 0.8 |

In cotton, chlorsulfuron also had a strong negative impact on root length. Although PESA salt alone increased root length, it was unable to overcome the negative effects of chlorsulfuron on root length (Table 16).

TABLE 16

Effect of PESA salt and chlorsulfuron on main root length and shoot length (cm) of cotton.

| Chlorsulfuron ppm | Root Length (cm) | | Shoot Length (cm) | |
|---|---|---|---|---|
| | 0 ppm PESA salt | 30 ppm PESA salt | 0 ppm PESA salt | 30 ppm PESA salt |
| 0 | 7.7 | 14.0 | 4.7 | 5.2 |
| 1 | 2.1 | 2.1 | 2.3 | 2.7 |
| 10 | 1.8 | 2.0 | 1.5 | 1.7 |
| 100 | 1.9 | 2.0 | 1.7 | 1.7 |

These results indicate that PESA salt does not protect either cotton or rice plants from the growth inhibiting action of chlorsulfuron.

Example 10

Rice seed treated with PESA was tested for its ability to protect rice from the herbicide Roundup WeatherMax® (glyphosate). After seed treatment, rice was seeded into soil previously treated with the Roundup WeatherMax®. The emergence of rice seedlings was counted daily and showed that PESA salt could protect the rice seedlings from glyphosate, at 90 μg/cm$^2$ (Table 17). This data confirms that seed treatment with PESA salt protects or safens rice from the negative effects of glyphosate herbicide on plant growth.

TABLE 17

Effects of PESA salt and Roundup ® (Glyphosate) on emergence of rice cv. Cheniere.

| Seed Treatment | Percent Emergence at 9 days after planting Glyphosate (μg/cm2) | | |
|---|---|---|---|
| | 0 | 23 | 90 |
| Control | 90 | 72 | 12 |
| 25 g PESA salt per 100 kg of seed | 80 | 84 | 28 |
| 50 g PESA salt per 100 kg of seed | 92 | 78 | 38 |

These results indicate that PESA salt protects rice plants from the growth inhibiting action of glyphosate.

In summary, PESA salt safens or protects plants from the negative effects of all herbicides tested except chlorsulfuron. The data for these examples are summarized below (Table 18).

TABLE 18

Herbicides tested and the effect of PESA salt on herbicidal activity

| Herbicide | Herbicide Chemical Class and MOA[1] | Effect of PESA on Herbicidal Activity | Example Number |
|---|---|---|---|
| Trifluralin | Dinitroaniline, Inhibition of microtubule assembly and cell division | PESA salt protected plants from herbicide activity | 1 |

TABLE 18-continued

Herbicides tested and the effect of PESA salt on herbicidal activity

| Herbicide | Herbicide Chemical Class and MOA[1] | Effect of PESA on Herbicidal Activity | Example Number |
|---|---|---|---|
| Pendimethalin | Dinitroaniline, Inhibition of microtubule assembly and cell division | PESA salt alone or in combination with GA3 protected plants from herbicide activity | 2 |
| Dithiopyr | Pyridine, Inhibition of cell division | PESA salt protected plants from herbicide activity | 3 |
| Clodinafop-propargyl | Aryloxyphenoxy-propionate, inhibition of acetyl CoA carboxylase | PESA salt protected plants from herbicide activity | 4 |
| Metalochlor | Chloroacetamide, MOA is not well understood | PESA salt protected plants from herbicide activity | 5 |
| Dicamba | Benzoic acid, auxinic herbicide whose MOA is not well understood | PESA salt protected plants from herbicide activity | 6 |
| Flumioxazin | Dicarboximide, inhibition of protoporphyrinogen oxidase | PESA salt protected plants from herbicide activity | 7 |
| Imazosulfuron | Sulfonylurea, inhibition of acetolactate synthase | PESA salt protected plants from herbicide activity | 8 |
| Chlorsulfuron | Sulfonylurea, inhibition of acetolactate synthase | PESA salt did not protect either rice or cotton plants from herbicidal activity | 9 |
| Glyphosate | Inhibition of EPSP synthase | PESA salt seed treatment protected rice from pre-emergence glyphosate application | 10 |

[1]Herbicide Chemical Class and MOA are based upon the Herbicide Handbook, Seventh Edition (Weed Science Society of America); Sprague and Hager, 2001. Utilizing herbicide site of action to combat weed resistance to herbicides. University of Illinois Extension, Champaign-Urbana, Illinois.

In conclusion, PESA salt provides significant protection or safening of plants from a range of herbicides. Those herbicides modes of action include inhibition of plant cell division, inhibition of acetyl CoA carboxylase, auxinic herbicides, an EPSP synthase inhibitor and inhibitors of protoporphyrinogen oxidase. However, PESA salt did not protect cotton or rice from the herbicidal effect of chlorsulfuron, a sulfonylurea herbicide.

The invention claimed is:

1. A composition for safening rice plant roots comprising N-(phenylethyl)succinamic acid (PESA) or its salts and pendimethalin.

2. The composition according to claim 1 where the N-(phenylethyl)succinatnic salt is sodium.

3. The composition according to claim 1 further comprising gibberellic acid.

4. A. method for safening rice plant roots comprising applying the composition of claim 1 to a rice plant or soil surrounding said rice plant.

5. A method of safening rice plant roots comprising applying N-(phenylethyl)succinamic acid (PESA) or its salts and pendimethalin to rice seeds.

* * * * *